United States Patent [19]

Bessman

[11] Patent Number: 4,509,695
[45] Date of Patent: Apr. 9, 1985

[54] TISSUE PULVERIZER

[75] Inventor: Samuel P. Bessman, Los Angeles, Calif.

[73] Assignee: Spectrum Medical Industries, Inc., Los Angeles, Calif.

[21] Appl. No.: 514,454

[22] Filed: Jul. 18, 1983

[51] Int. Cl.³ .................. B02C 19/08; B02C 19/12
[52] U.S. Cl. ............................ 241/2; 241/23; 241/66; 241/199.11; 241/DIG. 37
[58] Field of Search .......... 241/DIG. 37, 2, DIG. 27, 241/23, 169, 169.2, 199.11, 65, 66, 67

[56] References Cited

U.S. PATENT DOCUMENTS

| 2,161,998 | 6/1939 | Chott | 241/169.2 X |
| 3,172,546 | 3/1965 | Schreiner | 241/DIG. 37 X |
| 3,941,317 | 3/1976 | Kanor | 241/2 X |
| 4,307,846 | 12/1981 | Spelsberg | 241/2 X |
| 4,366,930 | 1/1983 | Trombetti, Jr. | 241/169 |

Primary Examiner—Mark Rosenbaum
Attorney, Agent, or Firm—Edgar W. Averill, Jr.

[57] ABSTRACT

A tissue pulverizer for pulverizing specimens of living tissues for facilitating chemical testing and the like. The pulverizer has a base, a guide member for emptying into a receiving tube and an elongated pestle member. The parts are cooled with liquid nitrogen and the specimen inserted, covered with the cooled pestle and frozen. The pestle member is then struck with a hammer to pulverize the frozen sample.

14 Claims, 6 Drawing Figures

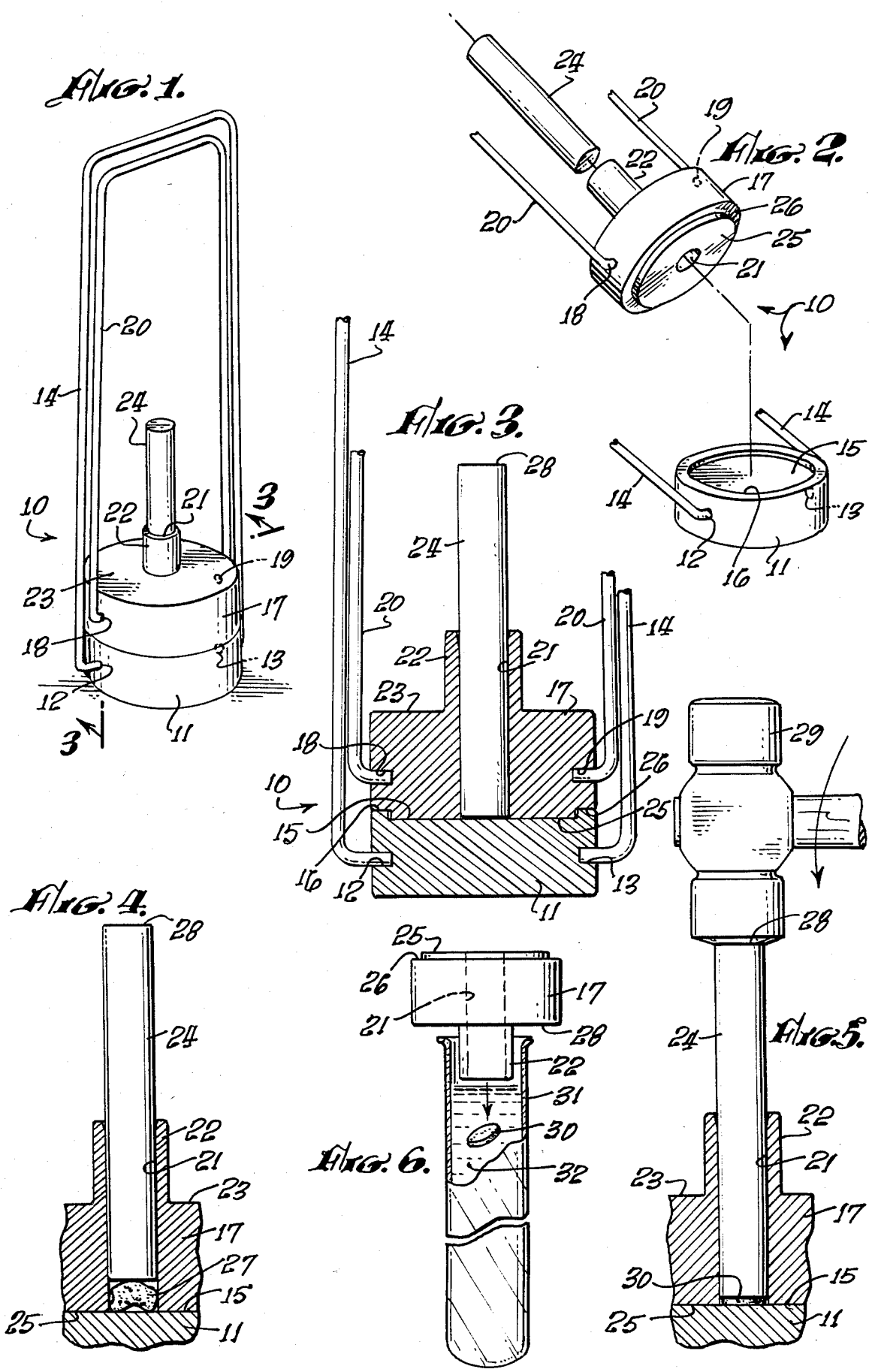

TISSUE PULVERIZER

BACKGROUND OF THE INVENTION

The field of the invention is laboratory equipment and the invention relates more particularly to equipment used for carrying out various biological testing. For many types of biological tests, it is necessary to comminute or pulverize these samples so that it may be subjected to processes such as leaching, dissolving or absorbing various materials. For many chemical tests, however, it is essential that the tissue be tested in a condition as close to its native state as possible since metabolism can occur to destroy the trace materials for which the testing is to be carried out. Such metabolism can occur in a very short span of time. It is common to use a protein precipitating liquid to stop such metabolism, but the process of pulverizing the sample often requires a span of time which permits an undesirable amount of such metabolism.

It has been common practice to subject a pair of forceps to liquid nitrogen and grasp the living tissue with the cold forceps to freeze the same before the sample is taken. The frozen tissue is then typically placed in a mortar and ground, and the ground tissue is then added to the precipitating solution. The transfer step, however, often brought about the undesirable metabolism. Although some benefit is obtained by freezing the precipitating solution and adding the frozen powdered tissue, permitting them to melt together, the problem of transferring the ground tissue to the test tube containing the precipitating medium remains.

SUMMARY OF THE INVENTION

It is thus an object of the present invention to provide an apparatus and a method for pulverizing specimens of living tissue for facilitating transfer of the pulverized material for chemical or other testing.

The present invention is for a tissue pulverizer which has a base member cooled to a temperature of at least as low as −150 degrees Centigrade. A guide member is removably mated with the upper surface of the base member, and the guide member is partable from the base member. The guide member has a guide passageway which terminates at the interface of the guide member and the base member, and the guide member is also cooled to a temperature of at least as low as −150 degrees Centigrade. An elongated pestle member is held in the passageway of the guide member and the pestle member is longitudinally movable in the passageway. The pestle member is sufficiently long so that it protrudes above the uppermost part of the guide member. Preferably, the pestle member is a cylindrical rod which fits in a cylindrical hole in the guide member and the hole in the guide member has a cylindrical extension which facilitates the passing of the sample from the guide member into a test tube or other container. The present invention also is for the process of using the above-described apparatus which further includes the steps of placing a specimen into the hole of the guide member and inserting the cooled pestle member into the hole. After permitting the specimen to become frozen, the upper end of the pestle member is struck with a hammer which pulverizes the frozen sample which is then transferred to the precipitating solution or other processing step.

BRIEF DESCRIPTION OF THE DRAWINGS

FIG. 1 is a perspective view of the tissue pulverizer of the present invention.

FIG. 2 is an exploded perspective view of the tissue pulverizer of FIG. 1.

FIG. 3 is a cross-sectional view taken along line 3—3 of FIG. 1.

FIG. 4 is an enlarged cross-sectional view showing the bottom portion of the chamber and a sample of tissue used with the tissue pulverizer of FIG. 1.

FIG. 5 is an enlarged, fragmentary, cross-sectional view showing the bottom part of the chamber and a pulverized tissue sample together with the top part of the pestle and a hammer useful with the process of the present invention.

FIG. 6 is a side view showing the upper portion of the tissue pulverizer of FIG. 1 inverted over a test tube.

DESCRIPTION OF THE PREFERRED EMBODIMENTS

The tissue pulverizer of the present invention is shown in perspective view in FIG. 1 and indicated generally by reference character 10. The pulverizer has a base member 11 which is preferably fabricated from stainless steel and is generally cylindrical in shape. Base member 11 has two holes 12 and 13 which support a handle 14. Handle 14 is optional but is useful for many operations where it facilitates the dipping of the apparatus in liquid nitrogen or other cooling medium. The top portion of base 11 is shown in FIG. 2 where it can be seen that a lowered central platform 15 is surrounded by a ring 16. This lowered platform permits the interlocking of base member 11 with the upper member 17 in a manner described more fully below.

The upper or guide member 17 is also generally cylindrical in shape and preferably fabricated from stainless steel. Guide member 17 has a pair of holes 18 and 19 which support handle 20. As above, handle 20 is optional and would not be needed if other grasping or transferring methods were available. Because the apparatus of the present invention is typically used in a very cold state, it is not possible to touch the cooled device with unprotected hands. Thus, the handles facilitate sample manipulation.

Guide member 17 has a central hole or passageway 21 seen best in FIG. 3. A relatively thin cylindrical extension 22 rises above the upper surface 23 of guide member 17. This extension facilitates the transfer of the pulverized sample to a test tube as indicated in FIG. 6 and described more fully below.

A pestle member 24 fits into hole 21 and extends down to platform 15 when upper guide member 17 is mated with base member 11. As can be seen in FIG. 2, base member 17 has a platform 25 which is surrounded by an annular groove 26. Platform 25 fits snugly against platform 15 as shown in FIG. 3 and ring 16 fits in annular groove 26. This interlocking of the base member with a guide member facilitates the pulverizing process and helps assure that platforms 15 and 25 are adjacent to one another before the sample is pulverized.

In use, the device is assembled as shown in FIG. 1 and immersed in liquid nitrogen or other cooling medium. After the device has been cooled to the temperature of liquid nitrogen (−195.8 degrees Centigrade), the apparatus is removed and the pestle 24 is removed from the hole 21. A tissue specimen 27 is dropped in hole 21 and pestle 24 is reinserted in hole 21. Because of the cooled mass comprising base member 11, upper or guide member 17 and pestle 24, the specimen 27 is quickly frozen. The upper surface 28 of pestle 24 is then struck with a hammer 29 which pulverizes the sample thereby creating a pulverized pellet 30.

The pulverizing process of the present invention is very effective even though the specimen may be taken from skin tissue, muscle tissue or other very tough substances. Since the freezing of the specimen to a very cold temperature turns it from a tough state to a brittle state, the impact with pestle 24 instantly creates a very finely divided pellet. This impact and pressure has another beneficial effect in the process of the present invention. That is the creation of a pellet because of the momentary melting caused by the extreme pressure resulting from the impact. As noted from the familiar phenomenon of ice melting under the blade of an ice skate, it is known that ice melts under pressure and this phenomenon can be used beneficially to create a pellet 30 which has integrity and may be readily transferred to the next processing step.

Turning now to FIG. 6, a test tube 31 is filled with a protein precipitating solution such as perchloric or tri-chloro acetic acid or the like. This solution inactivates enzymes to prevent metabolism and permits the preserving of trace amounts of chemicals which can give important clues to the nature of the tissue. For instance, it is well known that chemical tests can be far more accurate than microscopic tests in the early detection of cancer. Thus, the process of the present invention can be used to assist in the analysis of a sample taken from a liver or other organ. By chemical testing, a malignancy can be detected before the cells have multiplied sufficiently to be observable under a microscope.

As can be seen in FIG. 6, cylindrical extension 22 assists in guiding the pellet 30 into the precipitating solution 32. Even in the event that pellet 30 sticks in the bottom of hole 21, it can readily be forced out by inserting pestle 24 through hole 21. It is preferable that hammer 29 be a lead hammer or one formed from a polymer so that the upper surface 28 of pestle 24 is not damaged. Pestle 24 can be inserted with either end placed into guide member 17 and thus its upper surface should not be damaged. While the tissue pulverizer of the present invention has been shown in the drawings as a cylindrical device, it could, of course, be square, hexagonal or other shapes depending upon the method anticipated to handle the device. Furthermore while the device is shown as having interlocking upper and lower parts, it would still be usable if these parts were not interlocking although the interlocking feature does facilitate handling. If desired, the hole 21, although preferably a drilled, round hole, may be square, rectangle or other shape. While the cylindrical extension 22 is beneficial for transferring the sample, in many uses, this is not necessary and this feature can be eliminated. Furthermore, while the cooling method has been indicated as the immersing in liquid nitrogen, other cooling methods may, of course, be used, although liquid nitrogen is preferred.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A tissue pulverizer for pulverizing specimens of living tissue for facilitating chemical or other testing, said pulverizer comprising:
    a base member having an upper surface, said base member being cooled to a temperature of at least as low as −150 degrees Centigrade;
    a guide member having a bottom which is removably mated with the upper surface of said base member, said guide member being partable from the base member, said guide member having a guide passageway which terminates at the interface of the guide member and the base member and said guide member being cooled to a temperature of at least as low as −150 degrees Centigrade; and
    an elongated pestle member held in said passageway of said guide member, said pestle member being longitudinally movable in said passageway but having its longitudinal axis fixed with respect to said guide member and said pestle member being sufficiently long so that it protrudes above the guide member when the bottom of the pestle member is touching the base member said pestle member also being cooled to at least as low as −150 degrees Centigrade.

2. The tissue pulverizer of claim 1 wherein said base member is generally cylindrical in shape and has a generally flat upper surface.

3. The tissue pulverizer of claim 2 wherein said base member and said guide member interlock with one another.

4. The tissue pulverizer of claim 1 wherein said guide member has a vertical, cylindrical hole therethrough and said pestle member is a cylindrical rod.

5. The tissue pulverizer of claim 4 wherein said guide member has a narrowed, cylindrical extension formed above the upper surface of the guide member.

6. The tissue pulverizer of claim 1 wherein said base member has handle means.

7. The tissue pulverizer of claim 1 wherein said guide member has handle means.

8. The tissue pulverizer of claim 1 wherein said base member and said guide member both have handle means.

9. The tissue pulverizer of claim 1 wherein said base member is a cylinder having a flat bottom and a flat top having a raised ring about the periphery of the top, said guide member is a cylinder having a flat bottom having an indented groove about its periphery so that it mates with the top of the base member and said guide member has a cylindrical hole along its vertical axis.

10. The tissue pulverizer of claim 9 wherein said guide member has a thin, hollow cylindrical extension above the hole therein extending above its upper surface.

11. A process for pulverizing living tissue comprising the steps of:
    cooling a base member to at least −150 degrees Centigrade;
    cooling a guide member which has a hole therethrough to at least −150 degrees Centigrade;
    cooling a pestle member to at least −150 degrees Centigrade;
    placing the guide member and the base member together so that the hole in the guide member terminates at the base member;
    placing a specimen of living tissue into the hole in the guide member;

inserting the cooled pestle member into the hole in the guide member;

waiting a length of time sufficient for the specimen to become frozen;

striking the upper end of the pestle with hammer means;

separating the base member from the guide member; and removing the resulting pulverized specimen.

12. The process of claim 11 further including the step of inverting the guide member over a test tube filled with a precipitating solution.

13. The process of claim 11 wherein said cooling steps are carried out by contacting the parts to be cooled with a liquified gas.

14. The process of claim 13 wherein said liquified gas is nitrogen.

* * * * *